(12) United States Patent
Wright (10) Patent No.: US 11,076,951 B2
(45) Date of Patent: *Aug. 3, 2021

(54) SYSTEMS FOR REPLACING A NATIVE HEART VALVE AND AORTA WITH A PROSTHETIC HEART VALVE AND CONDUIT

(71) Applicant: Edwards Lifesciences Corporation, Irvine, CA (US)

(72) Inventor: Gregory A. Wright, Orange, CA (US)

(73) Assignee: Edwards Lifesciences Corporation, Irvine, CA (US)

( * ) Notice: Subject to any disclaimer, the term of this patent is extended or adjusted under 35 U.S.C. 154(b) by 417 days.

This patent is subject to a terminal disclaimer.

(21) Appl. No.: 15/989,885

(22) Filed: May 25, 2018

(65) Prior Publication Data

US 2018/0271649 A1 Sep. 27, 2018

Related U.S. Application Data

(60) Continuation of application No. 15/445,651, filed on Feb. 28, 2017, now Pat. No. 10,307,248, which is a
(Continued)

(51) Int. Cl.
*A61F 2/24* (2006.01)

(52) U.S. Cl.
CPC .......... *A61F 2/2409* (2013.01); *A61F 2/2412* (2013.01); *A61F 2/2418* (2013.01);
(Continued)

(58) Field of Classification Search
CPC ........ A61F 2250/003; A61F 2250/0007; A61F 2250/001; A61F 2250/0017;
(Continued)

(56) References Cited

U.S. PATENT DOCUMENTS

| 4,218,782 A | 8/1980 | Rygg |
| 4,692,164 A | 9/1987 | Dzemeshkevich et al. |

(Continued)

FOREIGN PATENT DOCUMENTS

| EP | 0169259 A1 | 1/1986 |
| EP | 2476871 A2 | 7/2012 |

(Continued)

OTHER PUBLICATIONS

International Search Report from Corresponding PCT Application No. PCT/US2013/061467 dated Jan. 2, 2014.
(Continued)

*Primary Examiner* — Mohamed G Gabr
(74) *Attorney, Agent, or Firm* — Guy Cumberbatch; Hans P. Smith (57) ABSTRACT

A medical device includes an expandable conduit, a prosthetic heart valve and a delivery device, including a balloon catheter. The expandable conduit may include one or more inner or outer sleeves supported by a frame or stent. The sleeve(s) may be a bioprosthetic tissue wrapped, molded or sewn about the frame or stent. Coupled to an end of the expandable conduit is the prosthetic heart valve. The conduit and heart valve may be crimped on the balloon catheter for percutaneous deployment. The frame may be constructed of an expandable material for the conduit portion and an expandable material for the prosthetic heart valve portion. The prosthetic heart valve can be anchored at the native heart valve and then the conduit can be expanded into place to protect the aorta.

22 Claims, 6 Drawing Sheets

Related U.S. Application Data division of application No. 14/033,075, filed on Sep. 20, 2013, now Pat. No. 9,585,748.

(60) Provisional application No. 61/705,495, filed on Sep. 25, 2012.

(52) U.S. Cl.
CPC .......... *A61F 2/2433* (2013.01); *A61F 2/2436* (2013.01); *A61F 2210/0014* (2013.01); *A61F 2220/0016* (2013.01); *A61F 2220/0075* (2013.01); *A61F 2230/005* (2013.01); *A61F 2230/0006* (2013.01); *A61F 2230/0054* (2013.01); *A61F 2250/0048* (2013.01)

(58) Field of Classification Search
CPC ...... A61F 2250/0031; A61F 2250/0037; A61F 2250/0082; A61F 2250/0097; A61F 2250/0098; A61F 2/062; A61F 2/2424; A61F 2/2442; A61F 2/2454; A61F 2/2496; A61F 2/844; A61F 2/848; A61F 2/86; A61F 2/95; A61F 5/0076; A61F 2/0089; A61F 6/22; A61F 2017/00243
See application file for complete search history.

(56) References Cited

U.S. PATENT DOCUMENTS

| | | | |
|---|---|---|---|
| 4,747,848 A | | 5/1988 | Maini |
| 5,123,919 A | | 6/1992 | Sauter et al. |
| 5,139,515 A | | 8/1992 | Robicsek |
| 5,197,979 A | | 3/1993 | Quintero et al. |
| 5,376,112 A | | 12/1994 | Duran |
| 5,545,215 A | | 8/1996 | Duran |
| 5,693,085 A | * | 12/1997 | Buirge .................. A61F 2/0022 606/192 |
| 5,814,096 A | | 9/1998 | Lam et al. |
| 5,862,806 A | | 1/1999 | Cheung |
| 5,891,195 A | | 4/1999 | Klostermeyer et al. |
| 6,001,126 A | | 12/1999 | Nguyen-Thien-Nhon |
| 6,090,140 A | | 7/2000 | Gabbay |
| 6,264,691 B1 | | 7/2001 | Gabbay |
| 6,299,638 B1 | | 10/2001 | Sauter |
| 6,352,554 B2 | | 3/2002 | De Paulis |
| 6,390,447 B1 | | 5/2002 | Mosher |
| 6,482,228 B1 | | 11/2002 | Norred |
| 6,783,556 B1 | | 8/2004 | Gabbay |
| 6,875,230 B1 | | 4/2005 | Morita et al. |
| 6,976,952 B1 | | 12/2005 | Maini et al. |
| 7,018,404 B2 | | 3/2006 | Holmberg et al. |
| 7,258,698 B2 | | 8/2007 | Lemmon |
| 7,261,732 B2 | | 8/2007 | Justino |
| 7,422,603 B2 | | 9/2008 | Lane |
| 7,488,346 B2 | | 2/2009 | Navia |
| 7,575,592 B2 | | 8/2009 | Woo |
| 7,618,447 B2 | | 11/2009 | Case et al. |
| 7,625,403 B2 | | 12/2009 | Krivoruchko |
| 7,641,686 B2 | | 1/2010 | Lashinski et al. |
| 7,641,687 B2 | | 1/2010 | Chinn et al. |
| 7,686,844 B2 | | 3/2010 | Case et al. |
| 7,717,952 B2 | | 5/2010 | Case et al. |
| 7,806,920 B2 | | 10/2010 | Duran |
| 7,972,376 B1 | | 7/2011 | Dove et al. |
| 8,080,054 B2 | | 12/2011 | Rowe |
| 9,289,282 B2 | | 3/2016 | Olson et al. |
| 9,301,835 B2 | | 4/2016 | Campbell et al. |
| 9,498,317 B2 | | 11/2016 | Gautam et al. |
| 9,585,748 B2 | | 3/2017 | Wright |
| 9,844,436 B2 | | 12/2017 | De Paulis et al. |
| 10,307,248 B2 | * | 6/2019 | Wright .................. A61F 2/2409 |
| 2002/0177891 A1 | | 11/2002 | Parodi |
| 2003/0139805 A1 | | 7/2003 | Holmberg et al. |
| 2003/0187500 A1 | | 10/2003 | Jansen et al. |
| 2004/0193242 A1 | | 9/2004 | Lentz et al. |
| 2005/0143810 A1 | | 6/2005 | Dauner et al. |
| 2005/0222675 A1 | | 10/2005 | Sauter |
| 2005/0267559 A1 | | 12/2005 | De Oliveira |
| 2006/0085060 A1 | | 4/2006 | Campbell |
| 2006/0167386 A1 | | 7/2006 | Drake et al. |
| 2006/0271081 A1 | | 11/2006 | Realyvasquez |
| 2006/0276813 A1 | * | 12/2006 | Greenberg ............ A61F 2/2418 606/158 |
| 2007/0156234 A1 | | 7/2007 | Adzich et al. |
| 2007/0227544 A1 | | 10/2007 | Swann et al. |
| 2008/0147171 A1 | | 6/2008 | Ashton et al. |
| 2009/0093873 A1 | | 4/2009 | Navia |
| 2009/0157174 A1 | | 6/2009 | Yoganathan et al. |
| 2009/0171456 A1 | * | 7/2009 | Kveen ................... A61F 2/2418 623/2.11 |
| 2009/0192604 A1 | | 7/2009 | Gloss |
| 2009/0264993 A1 | | 10/2009 | Greenan |
| 2010/0030340 A1 | * | 2/2010 | Wolfinbarger, Jr. ........ A61F 2/4644 623/23.72 |
| 2010/0274351 A1 | | 10/2010 | Rolando et al. |
| 2011/0125244 A1 | * | 5/2011 | Roeder ..................... A61F 2/07 623/1.11 |
| 2011/0214398 A1 | | 9/2011 | Liburd et al. |
| 2011/0264201 A1 | | 10/2011 | Yeung et al. |
| 2011/0301688 A1 | | 12/2011 | Dolan |
| 2012/0010697 A1 | | 1/2012 | Shin et al. |
| 2012/0046726 A1 | | 2/2012 | Chuter |
| 2012/0179086 A1 | | 7/2012 | Shank et al. |
| 2016/0067042 A1 | | 3/2016 | Murad et al. |
| 2016/0081829 A1 | | 3/2016 | Rowe |
| 2016/0266004 A1 | | 9/2016 | Van Nest et al. |
| 2016/0270913 A1 | | 9/2016 | Campbell et al. |

FOREIGN PATENT DOCUMENTS

| | | |
|---|---|---|
| WO | 03007795 A2 | 1/2003 |
| WO | 2006004679 A1 | 1/2006 |
| WO | 2006/013234 A1 | 2/2006 |
| WO | 2013086132 A1 | 6/2013 |
| WO | 2013116785 A1 | 8/2013 |

OTHER PUBLICATIONS

Sundaram, Baskaran, CT Appearance of Thoracic Aortic Graft Complications, Cardiopulmonary Imaging, Clinical Observations, May 2007.
DiBartolomeo, Roberto, Bio-Valsalva Prosthesis: new conduit for old patients, Interactive Cardiovascular and Thoracic Surgery, Jul. 9, 2008.
Brochure, Stentless BioValsalva, New Innovative Self-Sealing Graft Technology Biplex.
Brochure, Biplex.
Brochure, Gelweave Anniversary.
Brochure, Gelweave Family.
Brochure, Gelweave Implant.
Brochure, Gelweave.
Koehler Elan valve.
Maselli et al. "Adjustable Sinotubular Junction for Aortic Valve Reimplantation Procedures," Ann Thorac Surg 2007;83:700-2, The Society of Thoracic Surgeons, Pisa, Italy.

* cited by examiner

SYSTEMS FOR REPLACING A NATIVE HEART VALVE AND AORTA WITH A PROSTHETIC HEART VALVE AND CONDUIT

RELATED APPLICATIONS

The present application is a continuation of U.S. patent application Ser. No. 15/445,651, filed Feb. 28, 2017, which is a divisional of U.S. patent application Ser. No. 14/033,075, filed Sep. 20, 2013 and now issued as U.S. Pat. No. 9,585,748, which claims priority under 35 U.S.C. § 119 to U.S. Provisional Application Ser. No. 61/705,495, filed Sep. 25, 2012. Each of these applications is incorporated by reference herein.

FIELD OF THE INVENTION

This application relates to methods, systems, and apparatuses for safely replacing native heart valves and aorta with prosthetic heart valves and conduits.

BACKGROUND OF THE INVENTION

Prosthetic heart valves have been used for many years to treat cardiac valvular disorders. The native heart valves (such as the aortic, pulmonary, tricuspid and mitral valves) serve critical functions in assuring the forward flow of an adequate supply of blood through the cardiovascular system. These heart valves can be rendered less effective by congenital, inflammatory, or infectious conditions. Such conditions can eventually lead to serious cardiovascular compromise or death. For many years, the definitive treatment for such disorders was the surgical repair or replacement of the valve during open heart surgery.

More recently, a transvascular technique has been developed for introducing and implanting a prosthetic heart valve using a flexible catheter in a manner that is less invasive than open heart surgery. In this technique, a prosthetic valve is mounted in a crimped state on the end portion of a flexible catheter and advanced through a blood vessel of the patient until the valve reaches the implantation site. The valve at the catheter tip is then expanded to its functional size at the site of the defective native valve, such as by inflating a balloon on which the valve is mounted.

Alternatively, the valve can have a resilient, self-expanding stent or frame that expands the valve to its functional size when it is advanced from a delivery sheath at the distal end of the catheter.

Balloon-expandable valves are commonly used for treating heart valve stenosis, a condition in which the leaflets of a valve (e.g., an aortic valve) become hardened with calcium. The hardened leaflets provide a good support structure on which the valve can be anchored within the valve annulus. Further, the catheter balloon can apply sufficient expanding force to anchor the frame of the prosthetic valve to the surrounding calcified tissue.

Often, heart valve problems, such as calcification, are associated with other heart problems such as aortic aneurysms. Although the delivery techniques described above address heart valve deficiencies to some extent, less invasive approaches to other heart problems are also desired. It would be particularly advantageous to be able to address both valve and aorta problems with a minimally invasive approach.

SUMMARY OF THE DISCLOSURE

A medical device for use in a heart having a native heart valve and a vessel extending therefrom is disclosed. The medical device includes a balloon-expandable conduit and a prosthetic valve. The delivery system includes a catheter having a balloon that is disposed inside the balloon-expandable conduit. The prosthetic valve is coupled to an end of the balloon expandable conduit. The prosthetic valve includes a self-expandable material configured to expand in a radially outward direction to frictionally engage at least a portion of the native heart valve. The frictional engagement prevents axial movement of the prosthetic heart valve and the balloon-expandable conduit relative to the native heart valve.

The balloon-expandable conduit may include a balloon-expandable tubular frame and a sleeve extending along and against the balloon-expandable frame. The self-expandable material may include a self-expandable tubular frame. The prosthetic valve may include valve leaflets supported within the self-expandable tubular frame. The balloon-expandable tubular frame and self-expandable tubular frame may be contiguously formed of a nitinol alloy. The self-expandable tubular frame may have an expanded memory shape.

The prosthetic valve may include an annular ring of woven material coupling the valve leaflets to the self-expandable tubular frame.

The sleeve may be formed of a bioprosthetic tissue. For example, the bioprosthetic tissue may include a bovine pericardium, a porcine pericardium or an allogenic or autogenic collagen matrix tissue. The bioprosthetic tissue sleeve may be glycerolized to facilitate dry storage.

The sleeve may also include a coating, such as a polymer or gel coating.

The medical device may also include a retractable sheath that defines an interior portion. The retractable sheath holds the prosthetic valve in a radially compressed configuration. The retractable sheath may include one or more radiopaque markers on its outer surface.

The balloon expandable material may be a plastically deformable metal material such as a stainless steel or nitinol.

Also included in the medical device may be one or more anchors. The anchors are coupled to and extend radially from an outer surface of the medical device. For example, the anchors may be supported by the balloon-expandable conduit or the self-expandable prosthetic valve. The anchors may include structure that facilitates tissue ingrowth, such as beads, dimples or fenestrations. The anchors may circumferentially spaced about the outer surface of the medical device.

A method includes delivering a balloon-expandable conduit coupled to a self-expandable prosthetic heart valve into a vessel extending from a native heart valve. Also, the self-expandable prosthetic heart valve is delivered into the native heart valve. The method also includes inflating a balloon disposed within the balloon-expandable conduit such that an outer surface of the balloon expandable conduit is urged toward the vessel. The self-expandable prosthetic heart valve is expanded within or near the native heart valve by axially moving a retractable sheath.

The delivering method may also include engaging the vessel or native heart valve with anchors coupled to the conduit or prosthetic heart valve.

A method of assembling a medical device includes coupling a self-expandable prosthetic heart valve adjacent a balloon-expandable conduit. Also, the method includes disposing a balloon and balloon catheter within an interior portion of the balloon-expandable conduit. The method further includes compressing the balloon-expandable conduit and the self-expandable prosthetic valve radially inwardly. The method also includes disposing at least the self-expandable prosthetic valve into an interior portion of a retractable sheath.

Coupling the self-expandable prosthetic heart valve adjacent the balloon-expandable conduit may include forming a contiguous frame, coupling a bioprosthetic sleeve to at least one end of the frame and valve leaflets to the other end of the frame. The other end of the frame is then formed to have an expanded memory shape.

DETAILED DESCRIPTION

Implementations of the present disclosure now will be described more fully hereinafter. Indeed, these implementations can be embodied in many different forms and should not be construed as limited to the implementations set forth herein; rather, these implementations are provided so that this disclosure will satisfy applicable legal requirements. As used in the specification, and in the appended claims, the singular forms "a", "an", "the", include plural referents unless the context clearly dictates otherwise. The term "comprising" and variations thereof as used herein is used synonymously with the term "including" and variations thereof and are open, non-limiting terms.

The inventor has observed a need for improved methods, systems, and apparatuses for delivering expandable prosthetic heart valves and conduits in a minimally invasive manner with a delivery device having a smaller diameter. The inventor has further recognized that transvalvular technologies provide opportunities to repair aortic pathologies, such as in the thoracic aorta or aortic arch. Conduits to supplement or replace the aorta may be delivered through minimally invasive routes, such as transapical or transvalvular routes.

The methods and devices described below may be used to replace native heart valves that have calcified leaflets associated with aortic stenosis and, at the same time, to repair defects in the aortic arch or thoracic aorta. Furthermore, the methods and devices desirably enable precise and controlled simultaneous delivery of the prosthetic valve and the conduit.

Disclosed below are representative embodiments of a medical device that can be secured within a native heart valve. For illustrative purposes, embodiments of the medical device are described as being delivered to the aortic valve and associated aorta. It should be understood that the disclosed medical device may be configured for use with other heart valves that have associated conduits.

Also, a range of aortic pathologies may be addressed, such as aortic or thoracic aneurysms, aorta stenosis, or aorta/thoracic dilatation.

Figure 1:
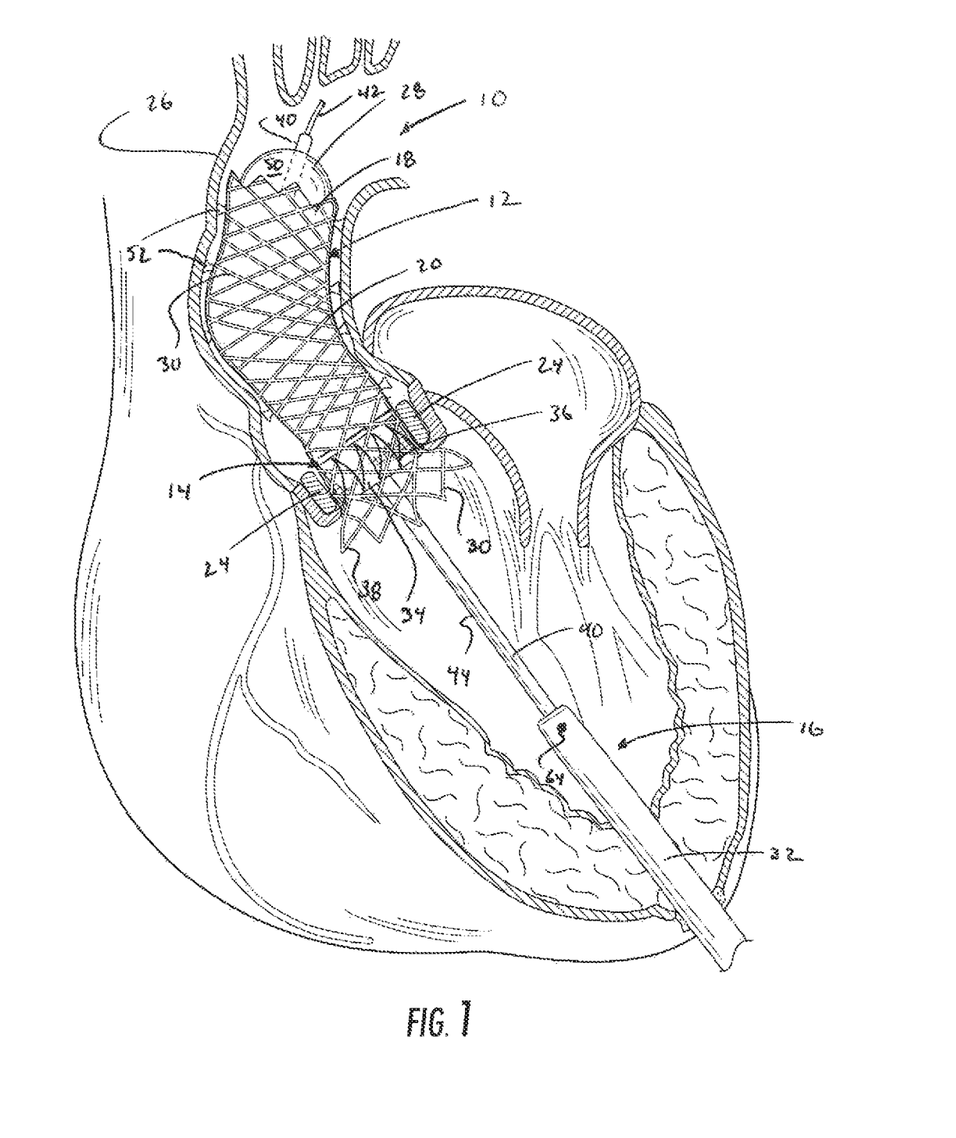
FIG. 1 is a perspective view of a medical device including transapical delivery of a coupled conduit and valve with the conduit being balloon expanded into an aorta.
Figure 3:
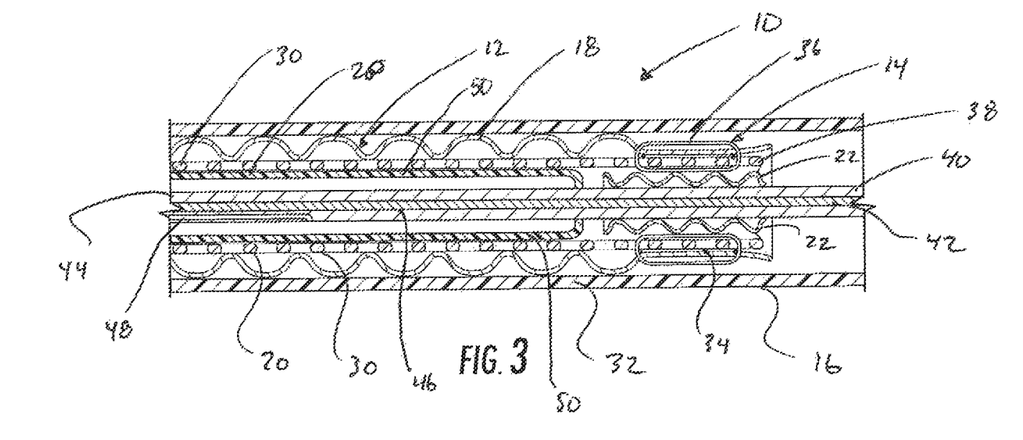
FIG. 3 is a sectional view of a delivery catheter holding a coupled balloon-expandable conduit and self-expanding valve.

As shown in FIG. 1, a medical device 10 includes an expandable conduit 12, a prosthetic heart valve 14 and a delivery device 16, including a balloon catheter 40. The expandable conduit 12 may include one or more inner or outer sleeves 18 supported by a frame or stent 20. The sleeve(s) 18 may be a bioprosthetic tissue wrapped, molded or sewn about the frame or stent 20. Coupled to an end of the expandable conduit is the prosthetic heart valve 14. For example, the prosthetic heart valve may include a portion of the frame 20 with soft tissue valve leaflets 22 sewn therein. As shown in FIG. 3, the conduit 12 and heart valve 14 may be crimped on the balloon catheter 40 for percutaneous deployment, or some other minimally invasive deployment approach, such as a transaortic or transapical approach.

Figure 2:
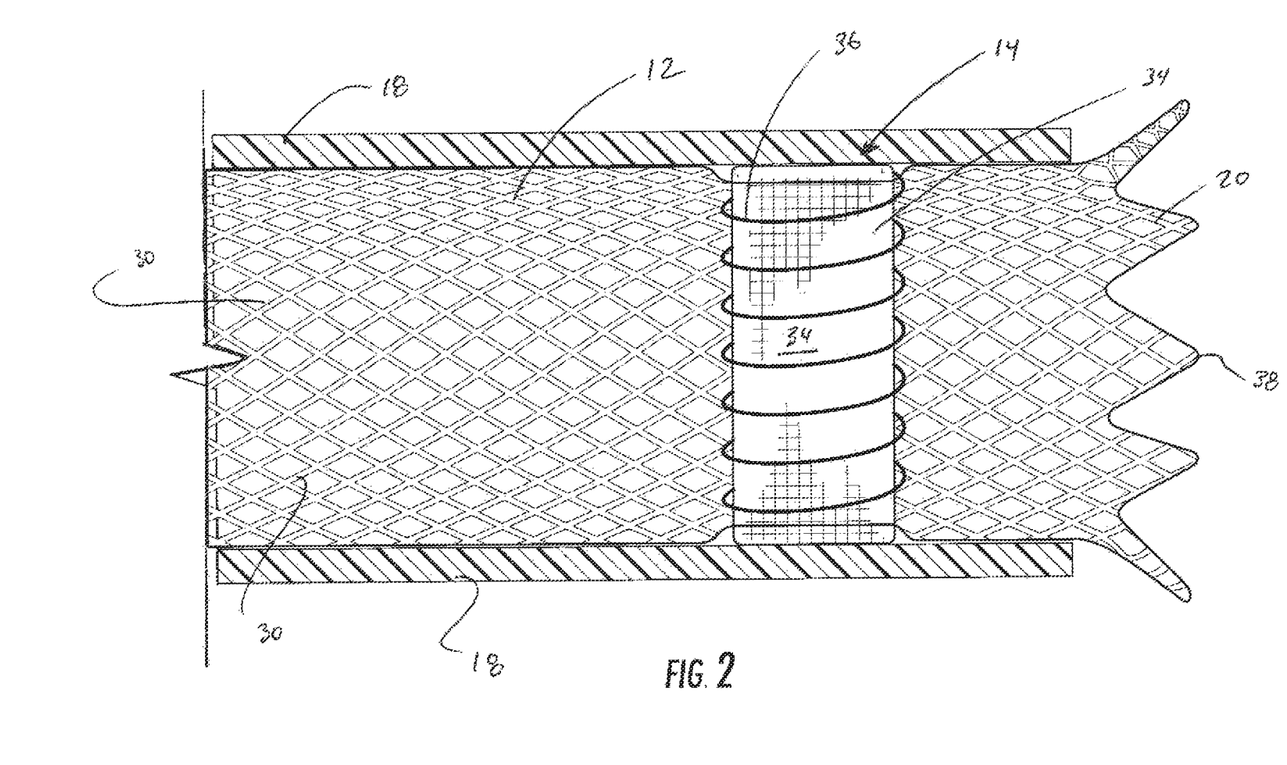
FIG. 2 is a partial sectional view showing a bioprosthetic sleeve extending over a stent frame holding an expandable tissue valve.

Advantageously, the frame or stent 20 may be constructed of a balloon-expandable material for the conduit 12 portion and a self-expandable material for the prosthetic heart valve 14 portion. As shown in FIG. 2, this allows the prosthetic heart valve 14 to first be anchored precisely at the native heart valve 24 and then, as shown in FIG. 1, the conduit 12 expanded into place to protect the ascending aorta 26.

Also advantageously, the self-expanding nature of the prosthetic heart valve 14 allows it to be mounted over a portion of the balloon catheter 40 that does not have a balloon 28. This provides for a lower diameter and easier delivery.

The device 10, including the conduit 12, prosthetic heart valve 14 and delivery device 16 can have multiple sizes accommodating biological variation in patient valve and aorta anatomy.

The frame or stent 20, as shown in FIGS. 1-4, may be comprised of a plurality of struts 30 that are interconnected to provide a lattice configuration with closed cells. The frame 20 may be comprised of a range of materials, including metals and plastics. For example, the frame may be comprised of a shape memory metal, such as a stainless steel or nitinol (nickel-titanium) alloy. Nitinol has the advantage of being able to withstand large strains and other deformations. Forming the struts 30 for metal frames 20 may include, for example, laser-cutting a nitinol or stainless steel stock tube to form the holes between the struts.

The frame 20 may be constructed in parts of the same or different materials and later welded, sewn or otherwise bonded together. For example, the balloon expandable portion of the stent 20 that makes up the conduit 12 may be constructed of a biocompatible stainless steel material cut from a stainless steel tube as described above. The lattice frame 20 formed from the stainless steel may then be mounted (with or without some initial expansion) over the balloon 28 for later plastic deformation by the balloon into the expanded shape.

The prosthetic heart valve 14 portion of the stent 20 may be constructed of nitinol, expanded into a deployed shape by a balloon and then heat treated to have an expanded memory configuration. This expanded memory configuration is assumed upon deployment from the delivery device 16, i.e., when a retractable outer sleeve or sheath 32 of the delivery device (as shown in FIG. 3) is withdrawn. After formation, both portions of the stent frame 20 may then be attached to each other by bonding, welding or having adjacent ends sewn to each other using the holes defined by the struts 30.

A particularly elegant solution (as shown in the figures herein) is to cut the entire frame or stent 20 out of a single tube of nitinol and then subject the nitinol to different treatments to selectively train axial portions for mixed expansion. For example, the cut nitinol tube may be partially expanded and heat treated at the prosthetic valve end to have an expanded memory shape. The remainder of the frame or stent 20 could be maintained in a cooled condition to avoid imprinting a memory shape or the memory shape may be the compressed condition. This compressed condition is then overcome by large plastic deformations from later expansion of the balloon 28. Advantageously, forming the stent 20 using differential techniques but the same monolithic materials avoids the need for later attachment, provides for a continuity of struts, improved structural integrity, etc.

As another alternative, the stent 20 may be entirely balloon expanded or entirely self-expanding. If entirely balloon expanded, a longer or larger balloon 28 may be used for simultaneous expansion of the entire conduit and valve combination. However, the combination of balloon and self expanding has particular advantages as described elsewhere herein.

Figure 4:
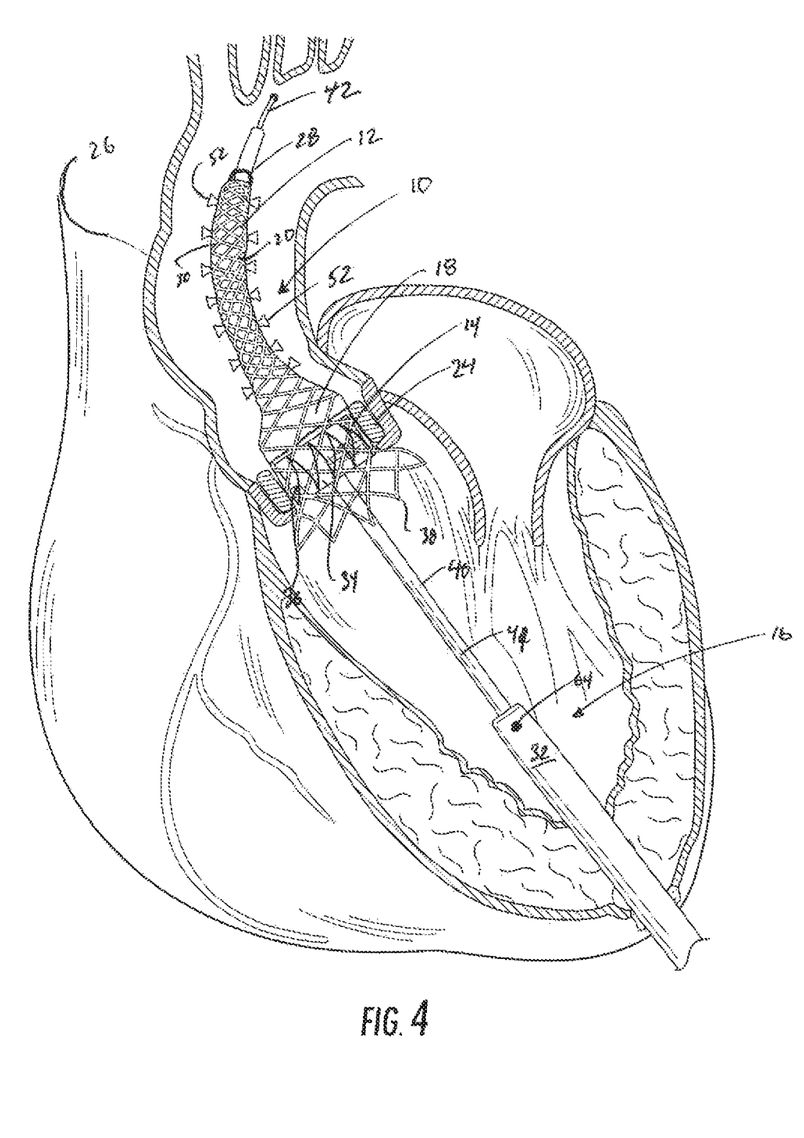
FIG. 4 is a perspective view of the medical device of FIG. 1 with the valve self-expanding into frictional engagement with a native heart valve to anchor the coupled conduit.

The sleeve 18, as shown in FIGS. 1 and 4, may extend within an inner surface of the frame 20 so as to protect the struts 30 of the frame from adhesions, clotting and other issues occurring from interaction with the blood flowing through the device 10. Alternatively, or in addition, the sleeve 18 may extend over the outside of the frame 20 or struts 30 so as to provide a surface on which to adhere to or fill the space between the frame and the surrounding native tissues of the aorta or valve of the heart. The sleeve 18 may also extend over both the inner and outer surfaces of the stent or frame 20.

Regardless of which surfaces it covers, the sleeve 18 is configured to provide a structure that helps to deflect and guide high pressure blood flow through the insufficient or compressed heart valve and the aneurismal aorta. Advantageously, the sleeve 18 and/or underlying frame 20 may have strategically placed openings, such as at the various branch vessels of the aorta (carotid or coronary arteries) to ensure perfusion of the heart and branch vessels.

The sleeve 18 may be constructed of a range of biological and/or synthetic materials and be applied or attached to the frame 20 in different ways. The sleeve may include, for example, bioprosthetic tissues such as bovine pericardium, porcine pericardium, or an allogenic and/or autogenic collagen matrix tissue. Bioprosthetic materials could be treated to withstand age and the environment, such as by being glycerolized to enable dry storage and improve lubrication. The bioprosthetic tissue could also be stored in glutaraldehyde.

As another option, polymers and gels (biological or synthetic) may be used for the sleeve 18. Non-biological polymers may be used for a solid polymer sleeve 18 or covering, such as silicone or polyurethane. The non-biological polymers may also include PET, PTFE or polyester films. Plant or animal derived collagen gels are an example of biological polymers or gels. Gels would generally be applied to some type of a substrate, such as an absorbable polymer substrate, a woven polyester, or bovine collagen matrix.

The sleeve 18 may also (optionally) be composed of a known graft material for treating aortic aneurysms, such as Dacron or PTFE cloth.

The sleeve 18 could also include combinations of some of the aforementioned materials. For example, the Dacron or PTFE cloth could be coated with the polymer or gel.

The different material types may be attached in different ways. For example, the sleeve 18, if comprised of a gel or polymer, may be applied as coating or as a molding or extrusion onto the surfaces of the frame 20. This facilitates a bonding attachment along a large portion of the surfaces of the frame 20, with some material extending into the holes defined between the struts 30.

The sleeve 18 may also be partially or wholly applied mechanically, such as by wrapping or sewing onto the frame 20. For example, a cloth of the sleeve 18 could be formed into a tube around the frame 20 by use of a longitudinal stitch to attach long edges of a rectangular, flat material. The same longitudinal stitch could extend between the struts 30 to anchor the sleeve 18 to the stent 20.

As another option, the cloth (Dacron or PTFE) sleeve 18 may have additional layers applied to it such as an outer or inner coating or layer of gel or polymer. The gel or polymer could be applied as a coating, molding or extrusion onto the cloth (before or after the cloth's attachment) to form the multiple layered sleeve 18.

The sleeve 18 may also optionally extend over the (and be considered part of) the prosthetic heart valve 14, as shown in FIGS. 2 and 3. Or, the sleeve 18 may terminate prior to reaching the axial end of the heart valve 14, as shown in FIGS. 1 and 4, even leaving a gap therein to facilitate blood flow to the coronary arteries extending from the aorta near the aortic valve root.

As shown in the cross-section of FIG. 3 and in FIG. 2, the prosthetic heart valve 14 includes an axial portion of the stent 20, soft tissue valve leaflets 22, a ring 34 and a plurality of stitches 36.

As described above, the portion of the stent 20 (or its own frame or stent if separately formed and attached) used to support the valve is a self-expanding material such as nitinol alloy with an expanded memory shape. A free end 38 of the stent 20 may terminate in a flared, crenellated memory configuration when deployed at the native heart valve 24, as shown in FIGS. 1 and 4. It takes this shape, for example, because there is no surrounding native tissue to constrain it from assuming the fully open memory shape. The flared shape may advantageously avoid interfering with blood flow from the heart.

Also advantageously, the expanded portion of the stent 20 exerts a radially outward force. Thus, the expanded stent 20 frictionally engages at least a portion of the native aortic valve 24. This substantially prevents axial movement of the prosthetic valve 14 and the balloon-expandable conduit 12 relative to the aortic valve 24.

The ring 34 extends around an outside (as shown in FIG. 2) or inside (as shown in FIG. 1) (or both) of the stent 20 and provides a structure for attachment and support of the valve leaflets 22. The ring 34 may be constructed of a polymer, tightly woven cloth material, such as a PET fabric or a PTFE fabric. Sutures or stitches 36 may be used to attach the cloth material ring 34 to the stent frame 20 by extending through the cloth material, over the stent frame on inside and outside surfaces and through the stent openings, as shown in FIG. 3. Additionally, the stitches 36 may attach the stent frame 20 and cloth ring 34 to the sleeve 18, whether the sleeve extends over the inside and/or outside surfaces of the stent frame.

The valve leaflets 22 are preferably constructed of a soft, pliable material such as thin bioprosthetic material, such as bovine pericardium. The valve leaflets are sewn, bonded or otherwise attached to the cloth ring 34 around its inside surface to form a one-way tricuspid valve structure. In this manner, with the attachments described above, the valve leaflets 22 are firmly anchored to the cloth ring 34 which is attached via stitches 36 or other means to the frame 20 and the sleeve 18. This prosthetic heart valve 14 construction then, as described herein, serves as the anchor for the remaining medical device 10 and for the conduit 12.

The stitches 36 may be constructed of a heavy suture material for a firm interconnection of the above-listed components. Various stitches are shown herein including long axially-directed loops (FIG. 2) that extend over ends of the ring 34. Or, as shown in FIG. 4, alternating zig-zag stitches may pierce and extend through the ring 34. Generally, the stitching pattern may be adapted to suit the thickness of the material layers, geometry of the stent and other variations described herein.

The delivery device 16, as shown in FIG. 3, shows the assembled medical device 10 ready for delivery of the conduit 12 and valve 14. The delivery device 16 includes the retractable outer sheath 32 and the balloon catheter 40 mounted within a central lumen of the outer sheath. The balloon catheter 40 includes a guide wire 42, an inflation catheter 44 and the balloon 28.

The guide wire 42 is a semi-flexible wire that is placed through the skin and up through the aortic valve 24 and into the ascending aorta in a transapical approach, as shown in FIG. 4. Conversely, the guide wire 42 may use a transfemoral approach by extending up the femoral artery and down the aortic arch through the aortic valve 24. Alternative approaches may also be used, including a more direct transaortic approach. Various approaches may or may not use a guide wire 42. Placement of the guide wire 42 may also use various devices such as an obturator to define gradually increasing diameter access holes, such as a transapical access hole.

The inflation catheter 44 defines a central lumen 46 by which it can be sleeved over the guide wire 42 once the guide wire is in place. The inflation catheter also includes an inflation lumen 48 which terminates within the walls of the balloon 28 mounted on the inflation catheter 44. At the proximal operator end, it may be attached to a gas or fluid supply for inflation of the balloon 28 during the deployment procedure. Construction and use of a balloon inflation catheter are well known to those of ordinary skill in the art.

The balloon 28, as shown in FIGS. 1 and 3, includes a balloon wall 50 that is configured to form a toroid cylinder shape extending along an axial portion of the inflation catheter 44. The balloon wall in FIG. 3 is crimped against the inflation catheter 44 and extends under the conduit 12 but stops short of the prosthetic heart valve 14. The balloon 28 may be directly beneath the frame 20 in some embodiments or may be under the sleeve 18 when the sleeve extends inside the frame in other embodiments, or in some combination of both.

The outer sheath 32 is another elongate, flexible tube that is configured to hold the expandable conduit 12 and the heart valve 14 in the crimped condition, as shown in FIG. 3. The prosthetic heart valve 14 extends around and is crimped onto the inflation catheter 44 not supporting the balloon 28. The expandable conduit 12 is crimped over the portion supporting the balloon 28. The lack of the intervening balloon 28 allows the leaflets 22 of the prosthetic heart valve to be compressed directly on the inflation catheter. This allows for a more uniform, smaller diameter of the medical device 10 in its crimped configuration. Smaller diameter delivery allows for use of the device 10 with a wider range of patients and less invasive procedures.

In the crimped condition, the soft tissue of the bioprosthetic sleeve 18 is notably bunched or crimped along the length of the delivery device 16. The soft tissue is then smoothed out during inflation and plastic deformation of the supporting frame or stent 20. Similarly, the valve leaflets 22 unfold or uncrimp, although under self-expansion by the shape memory effect of the supporting portion of the stent 20.

Also notable, is that the approach used for delivery may dictate whether the prosthetic heart valve is near the distal end of the outer sheath 32, such as for a transfemoral approach, or may be on a more proximal end (relative to the expandable conduit 12) of the outer sleeve (as shown in FIGS. 1 and 4) for the transapical approach.

Also, the delivery device 16 may include the use of radiopaque markers for targeting an aneurysm or the dilated portion of the diseased aorta or other vessel for easier implantation. Flush valves may also be included in the delivery device 16.

In addition, the retractable outer sheath 32 may include one or more radiopaque markers 64 supported on an outer surface of the sheath, as shown in FIG. 1. These markers 64 are designed to help position the delivery system and can be used to specifically position the system to target an aneurysm or dilated portion of a diseased vessel.

The medical device 10 may have additional features to facilitate its anchoring and later incorporation (by healing) into the surrounding tissue. For example, additional cloth PET portions could be used at the opposing ends extending around the outer frame 20 or sleeve 18.

The medical device 10 may also be stabilized by a plurality of metal anchors 52, as shown in FIGS. 1 and 4. The anchors 52 may extend radially about 2 mm to about 4 mm from the outer surface of the conduit 12 and/or the prosthetic heart valve 14. In addition, the anchors 52 may be circumferentially spaced apart along the length of the expandable conduit 12 or heart valve 14. In other embodiments, one or more anchors 52 may be defined on the frame or stent 20. Or the anchors may extend from the bioprosthetic sleeve 18.

The anchors may be constructed of a range of biocompatible materials, such as stainless steel, Nitinol or polymeric materials.

Figure 5:
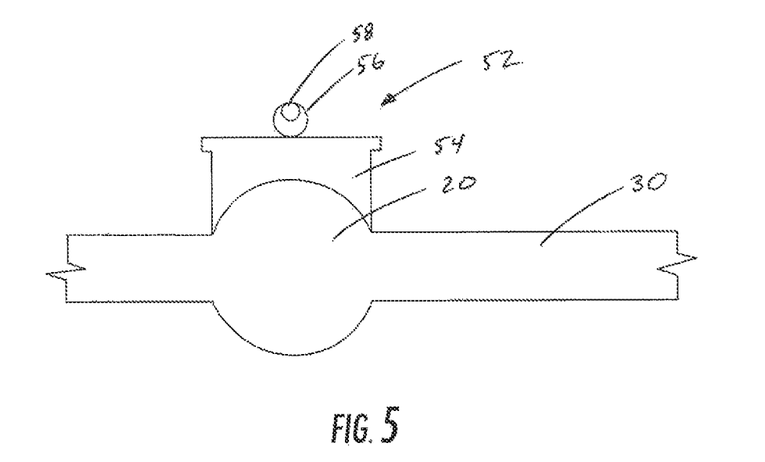
FIGS. 5-8 are enlarged schematics of various anchors that can be coupled to outer surfaces of the medical device for improved anchoring into native tissues.

FIGS. 5-8 illustrate various embodiments of the anchors 52. As shown in FIG. 5, the anchor 52 includes a base 54 topped by an irritation bead 56 defining a dimple 58. The base 54 is attached to the stent frame 20 (as shown) or directly to the sleeve 18. The irritation bead 56 is a spherical structure formed on or bonded to the base 54. It functions to irritate the surrounding tissue and induce a growth response to help anchor the conduit 12. The dimple 58 is a small golf-ball-like recess that further enhances irritation and tissue ingrowth.

Figure 6:
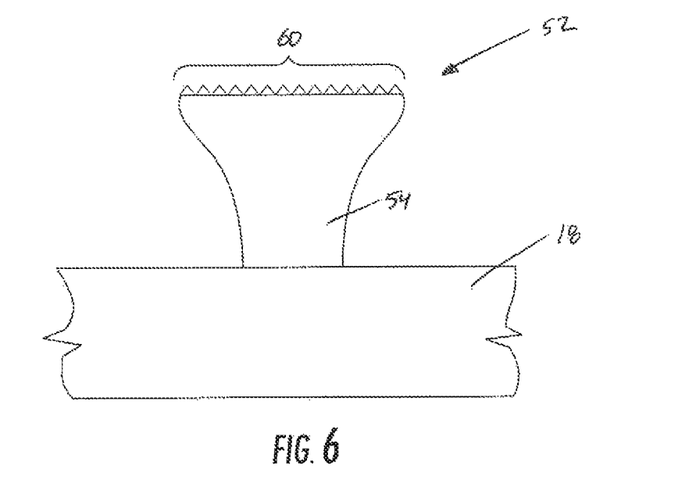

As shown in FIG. 6, the anchors 52 may include a base 54 that supports a discrete field of fenestrations 60 that extend radially outward. The fenestrations 60 are configured to frictionally engage tissue of the native vessel. These fenestrations, for example, may be formed as a knurled crisscross patterns of pyramidal structures by cold rolling the metal from which the anchors 52 are cut.

Figure 7:
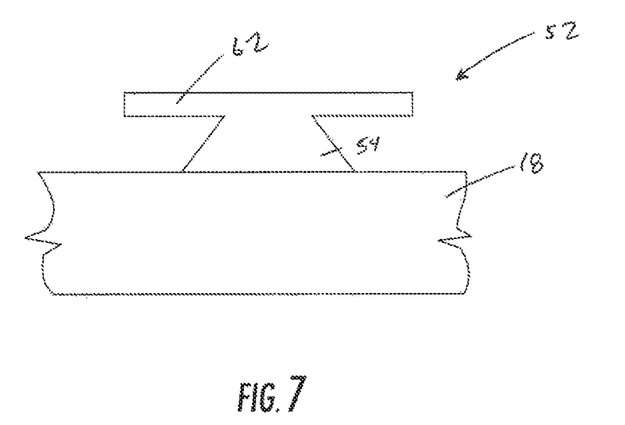
Figure 8:
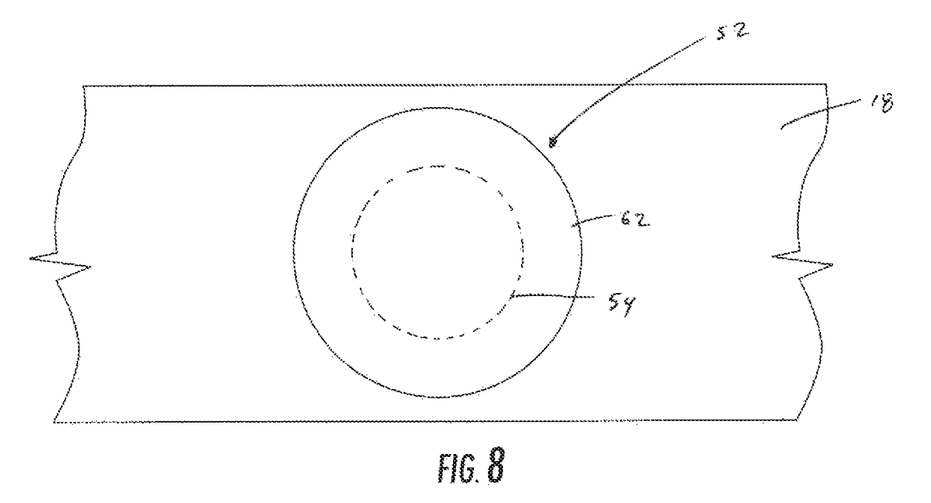

As shown in FIGS. 7 and 8, the anchors 52 may include a base 54 that supports a disc-shaped protrusion 62. The disc shape has a top surface that extends in the axial direction of the underlying frame 20. The diameter of the disc protrusion 62 is larger than the supporting base 54. This shape facilitates its anchoring on the tissue walls. The tissue becomes lodged under the disc 62, between it and the base 54 or underlying conduit 12.

In another embodiment, each of the anchors 52 may include a plurality of arms that extend outwards and are configured to frictionally engage the surrounding tissue.

A method of construction of the expandable conduit 12 and the prosthetic heart valve 14 may include coating or covering the interior surface, exterior surface, or both of the frame or stent 20 with (1) a bioprosthetic tissue, which may be selected from the group comprising a bovine pericardium, porcine pericardium, and allogenic/autogenic collagen matrix tissue, (2) a polymer, (3) a gel applied to a substrate or (4) a cloth, such as PTFE or Dacron, to form the sleeve 18. The sleeve 18, if it has a biological component, may then be glycerolized to facilitate dry storage. The method may also include applying a covering, such as a cloth, and coating the covering with a gel or polymer to form multiple layers.

During assembly of the medical device 10, the expandable conduit 12 is sleeved over the inflation catheter 44 until over the balloon 28. The prosthetic heart valve 14 is also sleeved (as the expandable conduit 12 is sleeved) over the adjacent portion of the inflation catheter 44 without the balloon. The prosthetic heart valve 14 is in the expanded condition due to its shape memory properties while the expandable conduit 12 is still relatively compact. A crimper is then used to crimp the conduit and valve, and underlying balloon 28, which are inserted into the outer, retractable sleeve 32 of the delivery device 16.

During delivery, the guide wire 42 is placed through the transapical or transfemoral approaches, as described above, until part of the wire extends through the aortic arch 26 and part of the wire through the native heart valve 24. Some preliminary balloon expansion may be performed to open the calcified native heart valve.

The balloon catheter 40 is then sleeved over the guide wire and into the native heart valve 24 and aortic arch 26. The outer sheath 32 is withdrawn to allow the prosthetic heart valve 14 to expand into and compress the native heart valve 24, as shown in FIG. 4. The inflation lumen 48 of the inflation catheter 44 is used to pump saline or other fluid into the balloon 28, expanding the balloon wall 50 and surrounding conduit 12, as shown in FIG. 1. The anchors 52 impinge upon or engage the surrounding vessel and anchor thereto.

Advantageously, the medical device 10 described above can achieve a smaller compressed diameter to facilitate minimally invasive delivery of a prosthetic heart valve together with an attached conduit.

What is claimed is:

1. A system for use in replacing a native aortic heart valve of a human and repairing a defect in a section of the aorta leading to the aortic arch and contiguous with the native aortic heart valve, the system comprising:
   an elongated catheter having a balloon thereon;
   a retractable sheath defining an interior portion, the sheath being longitudinally movable over the catheter;
   an expandable/compressible valved conduit crimped over the catheter in a delivery state, the valved conduit having a length sufficient to extend from a first end configured to be secured at the native aortic heart valve to a second end configured to be attached within and extending along the aorta at least as far as the aortic arch, the sheath closely surrounding the valved conduit in the delivery state, and the valved conduit comprising:
      a prosthetic heart valve located at the first end comprising an expandable/compressible stent, the heart valve being configured to expand in a radially outward direction to frictionally engage at least a portion of the native heart valve, the heart valve having flexible valve leaflets that form a one-way flow structure therethrough;
      an aortic conduit coupled in series to the heart valve and extending to the second end comprising an expandable/compressible tubular frame and a tubular sleeve extending axially along and against the tubular frame and extending around the outside of the prosthetic heart valve, the tubular sleeve being configured to deflect and guide high pressure blood flow generated by the aortic valve, the aortic conduit being configured to expand in a radially outward direction to frictionally engage at least a portion of the aorta, the aortic conduit being configured to guide high pressure blood flow through the aortic conduit,
   wherein a first portion of the valved conduit is self-expandable and a second portion is balloon-expandable and the sheath must be retracted from around the valved conduit to permit expansion thereof.

2. The system of claim 1, wherein the first portion of the valved conduit is the heart valve, and the second portion of the valved conduit is the aortic conduit.

3. The system of claim 1, wherein the heart valve stent and tubular frame comprise a single stent contiguously formed of a Nitinol alloy.

4. The system of claim 1, wherein the heart valve stent and tubular frame are stents of two different materials coupled together.

5. The system of claim 1, wherein the heart valve is on a proximal end of the valved conduit relative to the catheter and the aortic conduit is on a distal end of the valved conduit relative to the catheter, and wherein the sheath must be retracted fully from around the valved conduit prior to self-expansion of the first portion thereof.

6. The system of claim 5, further including an outer tubular sleeve extending axially along and outside of the tubular frame to provide a tubular surface between the aortic conduit and surrounding native tissue.

7. The system of claim 1, wherein the heart valve further comprises an annular ring of a woven material coupling the valve leaflets to the tubular frame.

8. The system of claim 1, wherein the tubular sleeve is an inner tubular sleeve that extends axially along and within the tubular frame to provide a tubular barrier between the aortic conduit and blood flowing therethrough.

9. The system of claim 1, wherein the tubular sleeve comprises a collagen gel absorbed into a woven polyester substrate.

10. The system of claim 1, further comprising one or more anchors that are circumferentially spaced apart about an outer surface of the valved conduit and extend radially outwardly to facilitate attachment to surrounding tissue.

11. A system for use in replacing a native aortic heart valve of a human and repairing a defect in a section of the aorta leading to the aortic arch and contiguous with the native aortic heart valve, the system comprising:
   an elongated catheter;
   a retractable sheath defining an interior portion, the sheath being longitudinally movable over the catheter;
   an expandable/compressible valved conduit compressed radially inwardly onto the catheter in a delivery state, the valved conduit having a length sufficient to extend from a first end configured to be secured at the native aortic heart valve to a second end configured to be attached within and extending along the aorta at least as far as the aortic arch, the sheath closely surrounding the valved conduit in the delivery state, and the valved conduit comprising:

a prosthetic heart valve located at the first end comprising an expandable/compressible stent, the heart valve being configured to expand in a radially outward direction to frictionally engage at least a portion of the native heart valve, the heart valve having flexible valve leaflets that form a one-way flow structure therethrough; and an aortic conduit coupled in series to the heart valve and extending to the second end comprising an expandable/compressible tubular frame and a tubular sleeve extending axially along and against the tubular frame and extending around the outside of the prosthetic heart valve, the tubular sleeve being configured to deflect and guide high pressure blood flow generated by the aortic valve, the aortic conduit being configured to expand in a radially outward direction to frictionally engage at least a portion of the aorta, the aortic conduit being configured to guide high pressure blood flow through the aortic conduit, wherein the tubular frame and the heart valve stent are formed by a single stent contiguously formed of a Nitinol alloy, and wherein at least a portion of the single stent is self-expandable and the sheath holds that portion from expanding in the delivery state.

12. The system of claim 11, wherein the heart valve stent is self-expandable.

13. The system of claim 11, wherein the entire single stent is self-expandable.

14. The system of claim 11, wherein a second portion of the single stent is balloon-expandable, and the elongated catheter has a balloon thereon.

15. The system of claim 14, wherein the tubular frame is balloon-expandable and the balloon only extends within the aortic conduit and not the heart valve.

16. The system of claim 11, wherein the heart valve further comprises an annular ring of a woven material coupling the valve leaflets to the stent.

17. The system of claim 11, wherein the tubular sleeve is an inner tubular sleeve that extends axially along and within the balloon-expandable tubular frame to provide a tubular barrier between the balloon-expandable conduit and blood flowing through the aortic conduit.

18. The system of claim 17, further including an outer tubular sleeve extending axially along and outside of the balloon-expandable tubular frame to provide a tubular surface between the aortic conduit and surrounding native tissue.

19. The system of claim 11, wherein the tubular sleeve comprises a collagen gel absorbed into a woven polyester substrate.

20. The system of claim 11, wherein the tubular sleeve comprises bioprosthetic tissue selected from a group consisting of a bovine pericardium, a porcine pericardium, and an allogenic/autogenic collagen matrix tissue.

21. The system of claim 20, wherein the bioprosthetic tissue is glycerolized to facilitate dry storage.

22. The system of claim 11, further comprising one or more anchors that are circumferentially spaced apart about an outer surface of the valved conduit and extend radially outwardly to facilitate attachment to surrounding tissue.

* * * * *